United States Patent [19]

Galindo-Castro et al.

[11] Patent Number: 5,346,811
[45] Date of Patent: Sep. 13, 1994

[54] METHOD AND PRODUCTS FOR HUMAN PAPILLOMAVIRUS DETECTION

[75] Inventors: Iván Galindo-Castro; José L. Ramirez; Rafael R. Aldao, all of Caracas, Venezuela

[73] Assignees: Cerveceria Polar, Calif.; Universidad Central de Venezuela, Caracas, Venezuela

[21] Appl. No.: 820,412

[22] Filed: Jan. 15, 1992

Related U.S. Application Data

[63] Continuation-in-part of Ser. No. 733,034, Jul. 22, 1991, abandoned.

[51] Int. Cl.$^5$ .............. C12Q 1/70; C12Q 1/68; C07H 21/00; C07K 15/00
[52] U.S. Cl. .................. 435/5; 536/24.32; 435/6; 530/387.1
[58] Field of Search .......... 435/5, 6; 536/27, 24.3, 536/24.32; 530/387.1

[56] References Cited

U.S. PATENT DOCUMENTS

| | | | |
|---|---|---|---|
| 4,551,270 | 11/1985 | Danos et al. | 530/324 |
| 4,849,331 | 7/1989 | Lorincz | 435/5 |
| 4,849,332 | 7/1989 | Lorincz | 435/5 |
| 4,849,334 | 7/1989 | Lorincz | 435/5 |
| 4,886,741 | 12/1989 | Schwartz | 435/5 |
| 4,908,306 | 3/1990 | Lorincz | 435/5 |
| 4,983,728 | 1/1991 | Herzog et al. | 536/27 |

FOREIGN PATENT DOCUMENTS

| | | |
|---|---|---|
| 0294659 | 12/1988 | European Pat. Off. |
| 0402132 | 12/1990 | European Pat. Off. |
| WO88/06634 | 9/1988 | PCT Int'l Appl. |
| WO89/02934 | 4/1989 | PCT Int'l Appl. |
| WO90/02821 | 3/1990 | PCT Int'l Appl. |

OTHER PUBLICATIONS

Matsukura et al. (1986) Journal of Virology, vol. 58(3), "Cloning of Monomenic HPV Type 16 DNA Integrated Within Cell DNA from a Cervical Carcinoma", pp. 979-982.

Dartman et al. (1986) Virology, vol. 151, "The Nucleotide Sequence Genome Organization of HPV Type 11", pp. 124-130.

Schwarz et al. (1983) EMBO Journal, vol. 2(12), "DNA Sequence and genome organization of genital HPV66", pp. 2341-2348.

Seedorf et al. (1985) Virology, vol. 145, "Human Papillomevirus Type 16 DNA Sequence," pp. 181-185.

Seedorf et al. (1987) EMBO Journal, vol. 6(1) "Identification of early proteins of HPV type 16 and 18 in cervical carcinoma cells", pp. 139-144.

Polynucleotide 3'-End Labeling Kit Package Insert, Cat. No. 1362-372, Boehringe-Mannheim Biochemicals, Indianapolis, Indiana (Jul. 1991).

Boehringer Mannheim Biochemicals, vol. 9, No. 1 (Jan. 1992).

Demeter et al., *J. Eur. Epidemol.* 3:404-413 (1987).

Harlow, E. et al., Antibodies, A Laboratory Manual Cold Spring Harbor Laboratory, pp. 342-349 (1988).

Heiles et al., *BioTechniques* 6(10):978-981 (1988).

Innis et al., PCR Protocols, A Guide to Methods And Applications, Academic Press, Inc., San Diego, Calif. pp. 3-11 (1990).

Manos et al., *Cancer Cells* 7:209-214 (1989).

Rakoczy et al., *Diagnostic Cytopathology* 6(3):210-214 (1990).

Stoler et al., *Human Pathology* 17(12):1250-1258 (1986).

Dürst, M., in Papillomaviruses and Human Disease, Syrjänen et al., eds., Springer-Verlag, Berlin, pp. 398-399 (1988).

Ting et al., PCR Protocols: A Guide to Methods and Applications, Academic Press, Inc., San Diego, Calif. pp. 356-367 (1990).

Wickenden et al., *The Lancet* pp. 65-67 (Jan. 12, 1985).

Boehringer Technical Bulletin (Jan. 1992).

*Primary Examiner*—Margaret Parr
*Assistant Examiner*—Lisa Arthur
*Attorney, Agent, or Firm*—Sterne, Kessler, Goldstein & Fox

[57] ABSTRACT

The present invention provides a Human Papillomavirus (HPV) detection method, the results capable of being read on specimen slides through in situ hybridization techniques. The method is based on a pair of consensus polynucleotide probes which hybridize type-specifically with clinically important HPV viral types and is capable of distinguishing between malignant and benign HPV viruses. Compositions of the polynucleotide probes in detectably labeled form are also a part of the invention. For correlation of the present method with known polymerase chain reaction (PCR) detection of HPV, a PCR assay is described.

28 Claims, 5 Drawing Sheets

UNIVERSAL PROBE        MALIGNANT PROBE

HPV-Negative
Control

HPV-Positive
Universal Probe

HPV-Positive
Malignant Probe

Negative Control
Genomic probe

Positive Control
Genomic Probe

SEQUENCE LISTING ( 1 ) GENERAL INFORMATION:

(i i i) NUMBER OF SEQUENCES: 8

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:1:

GAACTTATTA CCAGTGTTAT ACAGG     25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:2:

ATATCAGATG ACGAGRACGA AAATG     25

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:3:

AGCCCTGTAT TGGTT     15

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:4:

ATGGTACAAT GGGC     14

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:5:

TGCTCGTGCA TTAGAATC     18

(2) INFORMATION FOR SEQ ID NO:6:

(i) SEQUENCE CHARACTERISTICS:

(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

GTTACCTACA CTGTCAAC    18

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

GTCATCTATG TAGTTCCAAC AG    22

(2) INFORMATION FOR SEQ ID NO:8:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

TGCATCTTCC TCTTCCTCGT GC    22

METHOD AND PRODUCTS FOR HUMAN PAPILLOMAVIRUS DETECTION

BACKGROUND OF THE INVENTION
CROSS-REFERENCE TO RELATED APPLICATION

This is a continuation-in-part of U.S. patent application Ser. No. 07/733,034 filed Jul. 22, 1991, now abandoned, the contents of which are fully incorporated herein by reference.

1. Field of the Invention.

This invention utilizes two artificially-synthesized consensus polynucleotides as type-specific viral probes for Human Papillomaviruses, the probes preferably being immunochemically detected by enzymatically-conjugated antibodies specific for the probes. In a preferred embodiment this invention relates to an in situ hybridization system for the non-isotopic detection, in cervical Papanicolaou smears, of most clinically important types of Human Papillomaviruses (HPVs) infecting the anogenital tract.

2. Related Art.

The Human papillomavirus, commonly known as HPV, has been implicated in the genesis of human cancer (Gissman, L., *Cancer Surv.* 161-181 (1984); Durst et al, *Proc. Natl. Acad. Sci. USA* 80:3812-3815 (1983)). Out of more than 57 identified viral types, a third appear to preferentially infect the mucosal epithelium lining the anogenital tract, and within this group, types 16, 18, 33, and 35 are high-risk and are associated with precancerous lesions. Types 6 and 11 cause benign condylomata acuminata (venereal warts), and are treated as low risk infections.

The common test for the analysis of HPV-related lesions is the Papanicolaou Stain, which combines simplicity and accurateness, but is deficient because acute viral infection is usually necessary for reliable detection. Commonly known as the "Pap Smear" after the inventor George Papanicolaou and the technique of smearing cervical scrapes on a glass slide, the histological procedure involves the staining of cells obtained from the ano-genital tract with hematoxylin, a nuclear stain. Papanicolaou, G. N., *Science* 95:438-439 (1942). Though a pioneering breakthrough in detection of cervical cancer, the histological staining procedure suffers from a lack of repeatability, and the results may even vary from lab to lab. Efforts have been made to further refine the staining procedure (Schulte, E., Standardization of the Papanicolaou Stain I. A Comparison of Five Nuclear Stains, *Analytical and Quantitative Cytology and Histology*, 12(3):149-156 (1990)), but standardized results may not become the rule. Also, the Pap Smear is not sufficiently predictive of impending HPV-induced neoplasias. In fact, it has been shown in one study that 25% of patients with advanced in situ carcinoma may present normal Pap smears a few years before diagnosis (Lorincz et al., *J. J. Virol.* 58:225-229 (1986)). Therefore, there is an urgent need for new diagnostic tools capable of earlier detection, preferably in an HPV type-specific manner. The ideal test would allow the physician to reveal the presence of high-risk HPV types at an early stage, when no damage to the host cell is yet apparent. The patients showing evidence of high-risk viral type infections could then be monitored more frequently, and treatment could begin at an earlier stage.

The serological tests aimed at detecting circulating anti-HPV antibodies are of limited utility and are difficult to implement, since no cell culture is available to provide HPV antigens in large quantities (Taichman et al., The Search for a Culture System for Papillomavirus, *J. Invest. Dermatol.* 83:2s-6s (1984)). Additionally, serological tests do not enable discrimination between vital types.

Immunocytochemical techniques using labeled antibodies have high detection limits, due in part to the low avidity of the antibodies. Only 57% of the biopsies with clear morphological changes have been positive with this type of test (Gupta, J. et al, "Detection of Human Papillomaviruses in Cervical Smears. A comparison of "in situ" hybridization, immunocytochemistry, and cytopathology," *Acta Cytol* 31:387-391 (1987).

The use of DNA or RNA probes is potentially promising. Since 1980 more than 16 viral genomes have been cloned and used as type-specific probes in the diagnosis of HPVs (Gissmann et al., Molecular Cloning and Characterization of Human Papillomavirus DNA Derived from a Laryngeal Papilloma, *J. Virol.* 44:393-400 (1982); Lorincz et al., Characterization of Human Papillomaviruses in Cervical Neoplasias and Their Detection in Routine Cervical Screening, In: *Banbury Report* 21: Vital etiology of cervical cancer, pp. 225-237, Peto, R., et al, eds., Cold Spring Harbor Laboratory (1986)). Thus, the genomic information necessary for the construction of polynucleotide probes is available. These published viral genomes have also provided standards for the classification of new HPV viral types according to the percent homology of the newly-discovered vital genome as compared to known genomes.

In situ hybridization of genomic probe material with HPV-infected nuclear cell material has recently been demonstrated. Wagner, D., Identification of Human Papillomavirus in Cervical Swabs by Deoxyribonucleic Acid In Situ Hybridization, *Obstetrics and Gynecology*, 64(6):767-772 (1984). In this study, Wagner et al. demonstrate dot-blot hybridization on cervical swabs using $^{32}P$-labelled whole human papillomaviruses 6, 11, 16 and 18. A high incidence of invasive carcinoma corresponded to positive labelling of those tissues samples with $^{32}P$-labelled HPV types 16/18. In this context, the label "in situ" may be misleading because the term is usually identified with a procedure performed "in place" usually meaning in the cell. This procedure requires transfer of the cell contents via dot-blotting to a nitrocellulose membrane, NaOH-induced cell lysis, baking at 80° C., then exposure to the hybridization mixture. The results are not available until the autoradiogram is available 1-5 days later.

HPV DNA probes have been used in different hybridization-based assays such as Southern (Rader et al., Atypical Squamous Cells: A Case-Series Study of the Association Between Papanicolaou Smear Results and Human Papillomavirus Genotype, *J. Reproductive Medicine* 35(4):291-297 (1991)) and hybrid Dot/Southern (Rakoczy et al., Detection of Human Papillomavirus in Reprocessed Routine Papanicolaou Smears by DNA Hybridization, *Diagnostic Cytopathology* 6(3):210-214 (1990)) assays to detect HPV DNA in clinically-derived tissue samples. Additionally, purified biopsy DNA (Hallan et al, "Detection and typing of human papillomavirus infection of the uterine cervix by dot-blot hybridization: Comparison of scrapes and biopsies," *J. Med. Virol.* 27:317-321 (1989)), and in situ hybridizations in preserved tissue specimens, that is, direct localization within the intact cell of those sequences complementary to the nucleic acid probes have been demonstrated (Heiles et al., "In situ" Hybridization with digoxigenin-labelled DNA of Human Papillomaviruses HPV 16/18 in HeLa and SiHa Cells, *BioTechniques* 6:978-981 (1988)). The blot assays of purified DNA involve complex experimental protocols, have poor sensitivity and do not provide information about the cell architecture and viral location. This information is important in diagnosing the type and extent of the infection. Conversely, in situ hybridization not only provides this information, but laboratory protocols will be familiar to the cytologist and histologist who are comfortable with the traditional Pap Smear.

SUMMARY OF THE INVENTION

The invention provides a DNA HPV viral detection system for high- and low-risk Human Papillomaviruses and for distinguishing the malignant types (16/18) from those commonly associated with benign lesions (6/11). This invention provides the physician with a method of specifically detecting HPV genomes in patients at early stages of viral development.

The system combines the advantages of the simple in situ hybridization methodology with the powerful specificity of polynucleotide probes, in a non-radioactive assay. Detection is preferably provided by the specific binding of enzyme-labelled antibodies that generate a colorimetric signal upon addition of a color-developing reagent to the antigen-labelled polynucleotide probes. Observation of a purplish coloration in the nuclear material through a light microscope is the detection method of choice. The method is sensitive, fast, and provides type-specific information about the virus. A wide spectrum of users, including classically-trained histologists, will find this procedure familiar.

The invention comprises a first polynucleotide molecule comprising the sequence:

5' GAACTTATTACCAGTGTTATACAGG 3' (SEQ ID NO. 1)

or a stably hybridizable fragment thereof, and a second polynucleotide molecule comprising the sequence:

5' ATATCAGATGACGAGRACGAAAATG 3'
(SEQ ID NO. 2)

or a stably hybridizable fragment thereof, wherein R=A or G.

The combined use of both probes (hereinafter "Universal Probe") allows detection of general vital incidence and may be used for routine screenings in much the same manner as Pap Smears. The simultaneous use of a composition including the two probes allows the detection of HPV Types 6, 11, 16 and 18 that are associated with anogenital lesions, whereas the use of Probe 2 alone permits the detection of those viruses associated with malignancy, i.e., HPV types 16 and 18 (see FIG. 1). Use of Probe 2 alone is termed the Malignant Probe.

The invention also includes the first and second polynucleotide molecules in detectable form, particularly labelled with a digoxigenin dUTP tail attached to the 3' terminus of said polynucleotide molecules. Anti-digoxigenin enzyme-linked antibodies localize to the digoxigenin-labeled probe, and generate a purplish concentrate upon reaction with X-phosphate/NBT.

The invention also includes a hybridization mixture comprising a sample containing HPV genetic sequences (e.g., cells with intact nuclei), a hybridization buffer, and a detectably labelled probe having the sequence of any one of the polynucleotides of claims 1 or 2, or a mixture of both.

The invention also includes a method of detecting HPV in a sample containing or suspected of containing genetic sequences of HPV, which comprises contacting the sample with a detectably labelled probe having the sequences of claim 1 or claim 2, or with a mixture of both, under appropriate hybridization conditions to stably hybridize the probe or probes to the sample, and detecting the label.

The invention also includes a kit compartmentalized to receive in close confinement one or more containers, which comprises in combination: a first container comprising the polynucleotide molecules of claims 1 or 2, or a mixture thereof, and a second container comprising one or more reagents capable of indicating the presence of the polynucleotide.

BRIEF DESCRIPTION OF THE DRAWINGS

FIG. 2 is in black and white; the contrast between the stained nuclei is the determining factor.

DETAILED DESCRIPTION OF THE PREFERRED EMBODIMENTS

Figure 1A:
FIG. 1 shows an autoradiogram of the resultant dot blot hybridization with the Universal and Malignant probes. 100 ng of cloned HPV genomes (HPVs 6, 11, 16 and 18) and 10 ug of non-infected Human DNA were blotted onto a nitrocellulose membrane. After hybridization, the complementary oligoprobes were color-developed as recommended by the "GENIUS KIT ®" manufacturer (Boehringer Mannheim Biochemicals Indianapolis, Ind., USA). The specificity of each polynucleotide probe is manifested. Human DNA is actually present but is negative for both probes.
Figure 1B:
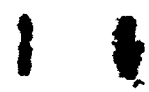

The polynucleotide molecule of the present invention encompasses various forms of nucleotide molecules. The term "polynucleotide" for purposes of this application encompasses both 2-deoxyribose and ribose nucleic acids. It also includes the various purine and pyrimidine bases that can be interchanged. The term "polydeoxynucleotide" includes two or more 2-deoxynucleotide molecules linked in 5'–3' manner. The chains may be circularized or linear. They may also be single or double stranded.

The polynucleotide sequence or probe will comprise at least one single stranded base sequence substantially complementary to or homologous with the sequence to be detected. However, such base sequence need not be a single continuous polynucleotide segment, but can be comprised of a fragment that will stably hybridize to the target sequence. When using polynucleotides as probes, hybridization conditions need to be controlled for successful detection of the target genomic sequence. Typically, hybridization with short (less than 200 bp) synthetic polynucleotides is carried out under stringent conditions, typically only 5°–10° C. below the melting temperature ($T_m$) of the hybrid. These short hybrids are far more prone to spontaneously unwind than are longer 200+ bp hybrids, so washing conditions are necessarily shorter and performed under less stringent conditions than hybridization.

The homologous region of the probe can be flanked at the 3'- and 5'-termini by nonhomologous sequences, such as those comprising the DNA or RNA of a vector into which the homologous sequence has been inserted for propagation. In either instance, the probe as presented as an analytical reagent will exhibit detectable hybridization at one or more points with sample nucleic acids of interest. Linear or circular single stranded polynucleotides can be used as the probe element, with major or minor portions being duplexed with a complementary polynucleotide strand or strands, provided that the critical homologous sequence or sequence fragments are in single stranded form and available for hybridization with sample DNA or RNA. Particularly preferred will be linear or circular probes wherein the homologous probe sequence is in essentially only single stranded form (see particularly, Hu and Messing, *Gene* 17:271–277 (1982)).

The polynucleotide probes of this invention are:

1: 5' GAACTTATTACCAGTGTTATACAGG 3'
(SEQ ID NO. 1), and stably hybridizable fragments thereof, and

2: 5' ATATCAGATGACGAGRACGAAAATG 3'
(SEQ ID NO. 2),

R being Adenine or Guanine, and stably hybridizable fragments thereof.

Probe 1 stably hybridizes to a sequence in the HPV 6 genome between and including bases 6341 and 6365, and in HPV 11 between and including bases 6326 and 6350. Both regions are in the L1 open reading frame (ORF) of each virus. Probe 2 hybridizes to the region of HPV 16 from bases 961 to 985, and in HPV 18 from bases 1007 to 1031. Both regions belong to the E1 ORF of each virus.

Practice of the analytical methods of the present invention is not limited to any particular hybridization format. Any conventional hybridization technique can be used. As improvements are made and as conceptually new formats are developed, such can be readily applied to carrying out the present compositions and methods. Conventional hybridization forms which are particularly useful include those wherein the sample nucleic acid or the polynucleotide probe is immobilized on a solid support (solid-phase hybridization) and those wherein the polynucleotide species are all in solutions (solution hybridization). Hybridization of the probes to the target vital nucleic acids may be accomplished by Southern, dot or slot blotting techniques, or other well-known hybridization technique. HPV DNA probes have been used in different assays such as Southern (Rader et al., Atypical Squamous Cells: A Case-Series Study of the Association Between Papanicolaou Smear Results and Human Papillomavirus Genotype, *J. Reproductive Medicine* 35(4):291–297 (1991)) and hybrid Dot/Southern (Rakoczy et al., Detection of Human Papillomavirus in Reprocessed Routine Papanicolaou Smears by DNA Hybridization. *Diagnostic Cytopathology* 6(3):210–214 (1990)) assays to detect HPV DNA in clinically-derived tissue samples. Additionally, purified biopsy DNA (Hallan et al., "Detection and typing of human papillomavirus infection of the uterine cervix by dot-blot hybridization: Comparison of scrapes and biopsies, "*J. Med. Virol.* 27:317–321 (1989)) may be used as a source of hybridizable DNA. A particularly preferred method of hybridization is in situ hybridization, that is, direct localization within the intact cell of those sequences complementary to the nucleic acid probes. In situ hybridization is well known in the art. See Heiles et al., "In situ" Hybridization with digoxigenin-labelled DNA of Human Papillomaviruses HPV 16/18 in HeLa and SiHa Cells, *BioTechniques* 6:978–981 (1988), incorporated herein by reference.

In the present invention, the length of Probes 1 and 2 is 25 base pairs. Thus, stringent conditions are preferred for in situ hybridization with target HPV sequences. Hybridization conditions may vary from 35° C. to 38° C. between 45 minutes to 4 hours. Preferably, hybridization occurs with a brief heat treatment sufficient to assist in the denaturing of the DNA, such as, for example, hybridization at 92° C. for 10 minutes, and then at 37° C. for 1 hour, preferably in 20% formamide. Other operable conditions will be known or apparent to those of ordinary skill in the art.

The invention also includes fragments of Probes 1 and 2 that are capable of stably hybridizing with the target sequences. The term "stably hybridizable fragments thereof" means any fragments of the claimed sequences that may stably hybridize to the 25 bp target genome listed herein under any hybridization conditions. An assay could easily be devised to determine whether fragments of the sequences of this invention will stably hybridize to the target HPV sequences, and at what temperature. As is known to those of ordinary skill, the shorter the polynucleotide probe, the more stringent the hybridization conditions must be. Greater stringency requires that the hybridization occur under higher temperatures, closer to the melting point ($T_m$) of the hybrid. A convenient method of calculating the $T_m$ for probe lengths of from 14 to as high as 60–70 bases is described in Sambrook, et al., Conditions for Hybridization of Polynucleotide Probes, in *Molecular Cloning-A Lab Manual*, 2d ed., p. 11.46, Cold Spring Harbor Press (1989). The following equation estimates the $T_m$ for short polynucleotide probes:

$$T_m = 81.5 - 16.6(\log_{10}[Na^+]) + 0.41(\% G+C) - (600/N),$$

where N=chain length. This equation will enable one of ordinary skill to calculate the $T_m$ for any length fragment of Probes 1 or 2, and adjust the hybridization conditions to find the optimum temperature for hybridization. Other factors that contribute to the stringency of hybridization include the G/C content, and the salt concentration.

The polynucleotide probes of the present invention hybridize to conserved homologous regions of the E1 ORF in several different types of HPV. The design of the sequences of the present invention has taken this observation into account. Probe 2 is degenerate in position 16 so that it may hybridize with both HPV types 16 and 18. Position 16 may be either Adenine (A) or Guanine (G), and is so designated by an "R" in the Sequence Listing. Probe 2 is considered a "consensus polynucleotide" because it is the typical nucleic acid sequence in which each position is the nucleotide found most often when many actual sequences are compared (See Rosen et al., Dictionary of Immunology, p. 52, Stockton Press, 1989).

Essentially any nucleic acid hybridization format can be followed for the purposes of the present invention in which either the hybrids formed between the probe and the sequence to be determined or the probe which has not hybridized with the sequence of interest are labelable with the selected label. As is known in the art, the labeling of such hybrids or unhybridized probe can be accomplished before or after the actual hybridization reaction. Normally, the probe is either labeled or labelable through a specific binding reaction or the formed hybrids are subsequently labeled, usually through a specific binding reaction. A central novel feature of the present invention is the advantageous application of the phenomenon of secondary labeling to the detection of nucleic acid hybridization.

The probe can be directly labeled in such a way that the hybrid itself is directly detectable. These methods are well known, and include radiolabeling, chemiluminescent labeling, fluorometric labeling, chromophoric labeling, and labeled antibody binding. Detection can be achieved by directly labeling the probe with a ligand as, for example, biotin which specifically binds to the protein streptavidin, and that protein can be a carrier for a chemiluminescent reaction component, as for example streptavidin linked covalently to alkaline phosphatase or horseradish peroxidase. All of these methods are well-known to one of ordinary skill in the art, and render the polynucleotide detectably labeled.

Direct radiolabeling of the probes of the present invention is possible by attaching radioactive isotopes such as $^{32}P$ to the phosphate groups of the phosphate-sugar backbone of the probe molecule. Those of ordinary skill in the art will appreciate that other radioactive labels such as 3H, or 125I are also possible. Once the probes are labeled radioactively, detection is accomplished by exposure to X-ray sensitive photographic film. Subsequent development of the film will enable one to visually detect the presence or absence of hybridization. These methods are well-known to those of ordinary skill in the art. See Sambrook, et al, Labeling of Synthetic Polynucleotides by Phosphorylation with Bacteriophage T4 Polynucleotide Kinase, in *Molecular Cloning, A Lab Manual*, 2d ed., pp. 11.31–32, Cold Spring Harbor Press (1989).

Enzyme-linked immunoassay is another technique useful for labeling the polynucleotide probes of the present invention. The antibody reagent used in the preferred embodiments of the present invention is principally characterized by its ability to bind to the hybrids formed between the probe and complementary sample nucleic acids through binding of the detectably labeled polynucleotide. The antibody reagent can consist of whole antibodies, antibody fragments, polyfunctional antibody aggregates, monoclonal antibodies, single-chain antigen-binding molecules, or in general any substance comprising one or more specific binding sites from an anti-hybrid antibody. When in the form of whole antibody, it can belong to any of the classes and subclasses of known immunoglobulins, e.g., IgG, IgM, and so forth. Any fragment of any such antibody which retains specific binding affinity for the hybridized probe can also be employed, for instance, the fragments of IgG conventionally known as Fab, F(ab'), and F(ab')$_2$. In addition, aggregates, polymers, derivatives and conjugates of immunoglobulins or their fragments can be used where appropriate.

The immunoglobulin source for the antibody reagent can be obtained in any available manner such as conventional antiserum, monoclonal antibody techniques, and recombinant genetic engineering of single-chain antigen-binding molecules. Antiserum can be obtained by well-established techniques involving immunization of an animal, such as a mouse, rabbit, guinea pig, sheep or goat, with an appropriate immunogen. The immunoglobulins can also be obtained by somatic cell hybridization techniques, such resulting in what are commonly referred to as monoclonal antibodies, also involving the use of an appropriate immunogen. Single-chain antigens are recombinantly engineered by insertion of a DNA segment coding for a linker polypeptide into a plasmid such that the linker will be expressed linking the two antigen-binding variable domains.

When the antibody reagent is used to detect hybrids, it will usually be labeled with an enzyme such as alkaline phosphatase, horseradish peroxidase, or glutaraldehyde, attached by suitable synthetic means. Alternatively, the antibody reagent can be detected based on a native property such as its own antigenicity. Further, antibody can be detected by complement fixation or the use of labeled protein A, as well as other techniques known in the art for detecting antibodies.

In a preferred embodiment the antibody reagent is labeled. The labeling moiety and the antibody reagent are associated or linked to one another by direct chemical linkage such as involving covalent bonds, or by indirect linkage such as by incorporation of the label in a microcapsule or liposome which is in turn linked to the antibody. Labeling techniques are well-known in the art and any convenient method can be used in the present invention.

A preferred method of detecting the hybridized polynucleotide probes of the present invention is to contact digoxigenin-labeled polynucleotide probes with anti-digoxigenin chromophoric antibodies. Digoxigenin is a steroid hapten that is linked via a spacer arm to the desired polynucleotide. Specifically, the spacer arm, 5'-deoxy uridinetriphosphate (dUTP), is chemically added to the 3' end of the probe using terminal transferase enzyme, as specified in the Polynucleotide 3'-End Labeling Kit, Cat. No. 1362-372, Boehringer-Mannheim Biochemicals, Indianapolis, Ind. Other deoxynucleoside triphosphates (dNTPs) may be used, including dATP, dGTP, dCTP, or dTTP. More than one dUTP may be added (Schmitz, G. G. et al, *Anal. Biochem.* 192:222 (1991)) if more Digoxigenin labels are needed to create a longer spacer arm for enhanced detectability. Detection of the Digoxigenin-dUTP-labeled hybrid is accomplished by contacting antidigoxigenin polyclonal antibodies labeled with polymerized alkaline phosphatase to the dUTP-coupled digoxigenin located on the probe. The probe-antibody complex develops an enzymatically-coupled purplish color precipitate wherever the probes hybridize upon contact with 5-bromo-4-chloro-3-indolyl phosphate (X-phosphate) in combination with nitro blue tetrazolium (NBT). One of ordinary skill will realize the precise concentrations and amounts to use of X-phosphate/NBT. See Sambrook, et al, Screening of Expression Libraries With Antibodies and Polynucleotides, in *Molecular Cloning, A Lab Manual,* 2d ed., p. 12.20, Cold Spring Harbor Press (1989). Additionally, the "GENIUS KIT ®" (Boehringer Mannheim Biochemicals, Indianapolis, Ind.) gives full directions on color development. The intense color development achieved by this means, together with the optimum penetrability of short, 25-bp oligoprobes to the nucleus, produces a very strong chromophoric signal even when relatively few copies of HPV are integrated into the genome.

One of ordinary skill will appreciate that other enzymes may be coupled to the bound antibodies for purposes of detection, including horseradish peroxidase and glutaraldehyde, and corresponding color-developing reagents applied. Specifically, the chemiluminescent reagent "LUMI-PHOS 530 ®", LuminGen, Inc., Detroit, Mich., allows the detection of hybrids on conventional X-ray film. Alternatively, other antidigoxigenin conjugates that would be suggested to one of ordinary skill include the fluorescers anti-digoxigenin-rhodamine, and anti-digoxigenin-fluorescein; and for electron microscopy anti-digoxigen in-(second antibody conjugated to gold).

The use of chromophoric labels can be detected by sight or by conventional means, such as by a light microscope. Recordation is by conventional color microphotography. Fluorescent or chemiluminescent labels emit light that may be detected by sight or by photomultiplier tube. Gold-conjugated labeling is used in electron microscopy to detect hybridization and to image the larger morphological features of the infected cell. Radiolabeled probes may be exposed to X-ray sensitive film.

In the present invention certain aspects of the detectably labeled polynucleotide probe are immunogenic. For instance, in the previous discussion the digoxigenin-dUTP spacer arm is recognizable by anti-digoxigenin antibodies or fragments thereof. Thus, for purposes of this invention and in this context, the digoxigenin-dUTP moiety is an antigen. Similarly, in certain situations the dNTP tail can be an antigen. It is well-known that antibodies that are raised in an appropriately stimulated host will produce antibodies specific for epitopes of the antigen. The dNTP tail may present sufficient size to present epitopes recognizable by antibodies, and thus offer another method of labeling the hybrid.

The hybridization mixture of the present invention includes a sample containing or suspected of containing HPV DNA or RNA sequences, a hybridization buffer, and a detectably labeled probe having the sequence of either or both Probes 1 and 2. More specifically, the sample may be a tissue sample obtained via scraping of epithelium from any area that may harbor HPV. Cervical or vulval scrapings obtained during gynecological exam, laryngeal scrapings obtained from the throat, penile scrapings, or cells obtained from archival sources may provide the requisite sample cells.

The hybridization buffer of the present invention may comprise any buffer solution that enables binding of the polynucleotide probes to the target sequences. There are many variations of such buffers. Variables that should be considered when selecting an appropriate buffer are solvent and temperature, volume of solvent and length of hybridization time, degree and method of agitation, use of pre-hybridization solution, blocking agents (to block attachment of probes to non-specific surfaces), concentration of probe and its specific activity, use of PEG or Dextran sulfate to increase effective concentration of probes in solution, and the stringency of washing following hybridization. Various guidelines are available in the public domain for the construction of hybridization solutions. See, e.g. Sambrook, et al., Hybridization of Radiolabeled Probes, in *Molecular Cloning-A Lab Manual,* 2d ed., vol. 2, pp. 9.47–9.51, Cold Spring Harbor Press (1989).

A preferred method of detecting HPV comprises contacting a sample with a detectably labeled probe, or a stably hybridizable fragment thereof, having the sequences of Probe 1 or 2, or with a mixture of both, under appropriate hybridization conditions to stably hybridize the probes or probe fragments to the sample, and subsequently detecting the label. The label may be incorporated directly into the unique sequences of this invention or labeling may occur post-hybridization, both methods being outlined in greater detail elsewhere in this specification. The type of label is also not limiting, and many types of labels are discussed herein. A preferred label of the present invention includes immunolabeling the hybrid with an anti-digoxigenin-dUTP antibody, the antibody itself being conjugated to an enzymic label, specifically alkaline phosphatase. Thus, visualization of the labeled hybrid occurs when a chromophoric reaction is completed by the addition of an oxidant or other reactant, specifically X-phosphate/NBT, to the antibody-localized hybrid.

Another preferred mode of the present invention is in situ cytohybridization. As used in the context of the present invention, "in situ" means that the hybridization is performed with the genomic material still present in the cell nucleus. The smeared cells, having been fixed to the glass slide, are contacted with a series of solutions and the probes hybridize to the target sequences (if present) in the cell. The results are visualized directly. This method preserves the gross morphological features of the HPV-infected cell, allowing the cytologist another verifying indication of infection.

The present invention also includes a kit, which contains all the necessary elements to carry out the assay described herein. Specifically, the kit contains, in close confinement, one or more containers which comprise a first container comprising the polynucleotide molecules of claims 1 or 2 or a mixture thereof, and a second container comprising one or more reagents capable of indicating the presence of the polynucleotides.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of the container can be added in a quantitative fashion from one compartment to another. Such containers will include a container for polynucleotide solutions, for antibody solutions, for radiolabels, for enzymes, fluorochromes or chemiluminescent agents to couple to the antibodies, for color-developing reagents such as X-phosphate/NBT, and containers for phosphate buffed saline, prehybridization and hybridization solutions, and other buffers.

The application of the polymerase chain reaction to HPV identification has been successfully applied to numerous HPV types. Although the individual genome of each HPV is unique, they share interspersed regions of DNA homology, particularly within the E1 and L1 open reading frames (ORFs). Although many HPV types have been identified, the complete DNA sequences of only five have been reported. By comparing the DNA sequences of genital HPV types 6, 11, 16 and 18 it is possible to identify regions of homology. From such regions are designed sets of consensus PCR primers that will amplify distinct regions from many of the genital HPVs. This method was first reported by Manos et al in 1989, and is more fully described by Manos and Ting in Detection and Typing of Genital Human Papillomaviruses, in *PCR Protocols-A Guide to Methods and Applications,* Innis et al., eds., pp. 356–367, Academic Press, Inc., San Diego, Calif. (1990).

This invention describes a PCR-based assay for correlating the in situ hybridization results with the established PCR type-sensitive detection assay. Table I (see Example 3) shows the Forward Primers that have been constructed for this purpose. Table II shows the Reverse Primers. Example 3 describes the steps necessary to perform the assay. This assay was designed to detect not only the presence of HPV viral genomes but to show the vital type, according to the size of the amplified DNA fragments (see FIG. 5). Six polynucleotides (Multiplex Primers) were used to prime the thermoresistant DNA polymerase during the PCR assay, and the sizes of each specific amplified product are also listed in Tables I and II.

Tables I and II show the main features of the PCR assay, including the set of polynucleotide primers used to prime the polymerization of the specific amplification target. There are a pair of forward primers, one for HPV6/HPV11 and the other for HPV16/HPV18. A unique reverse primer is necessary for each HPV type, so four reverse primers are shown in Table II. The tables also show the target genome sequence according to the base assigned in the original reported sequence (Schwarz et al., *EMBO J.* 2:2341–2348 (1983); Dartmann et al., *Virol.* 151:124–130 (1986); Seedorf et al., *Virol.* 145:181–185 (1985); and Cole et al., *J. Mol. Biol.* 193:599–608 (1987)). All primers target to regions within the E1 and E2 ORFs, and generate fragment sizes ranging from 222 bp to 809 bp.

The following examples are illustrative, but not limiting, of the compositions and methods of the present invention. Other suitable modifications and adaptations of the invention as well as the variety of conditions and parameters normally encountered in clinical assay designs and which are obvious to those skilled in the art are within tile spirit and scope of the invention.

All references cited herein are incorporated by reference into the disclosure of this specification.

EXAMPLES

Example 1

In situ Hybridization

The detailed protocol for in situ hybridization using the probes of the present invention is described as follows:

1) Spread a vaginal, vulval or penile cellular swap over a limited area (25×25 ram) on a specimen slide and fix with hair spray. (The contents of the hair spray is, in general, a mixture of butane, propane, isobutane, vinyl acetate, crotonic acid, vinyl neodecanate copolymers, lauramide, lanomide DEA, dimethycone, aminomethylpropanol and fragrance in 40% alcohol (or ethanol). Commercially available hair spray is suitable.) Locate the sample slides in a staining jar (groups of 20 slides may be easily accommodated).

2) Wash the fixed cells with 95% ethanol for 15 minutes.

3) Refix the cells with 4% paraformaldehyde in 1× phosphate buffered saline (PBS) for 15 minutes at 37° C.

4) Remove the remaining liquid and leave to air dry at 37° C.

5) Incubate in 0.2N HCl for 15 minutes at 25° C.

6) Wash the slides with 2× SSC (20× SSC: NaCl, 3M; Nacitrate, 0.3M; pH 7.0) for 15 minutes.

Figure 2A:
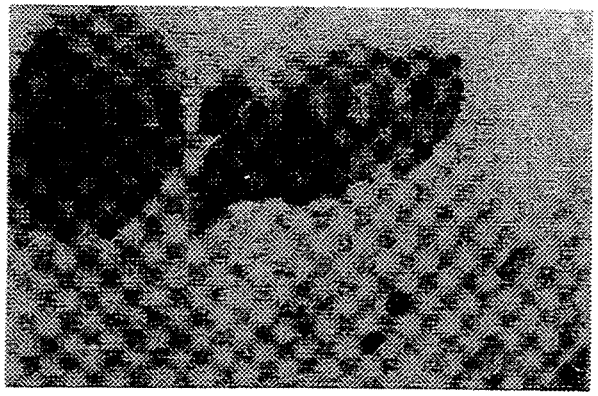
FIG. 2 shows a photocopy of a photomicrograph of positive and negative reactions of in situ hybridization of HPV-infected and non-infected tissues. The purplish accumulation (or its absence) in the nuclei of cells is the criterion to be evaluated by the cytologist/histologist.
Figure 2B:
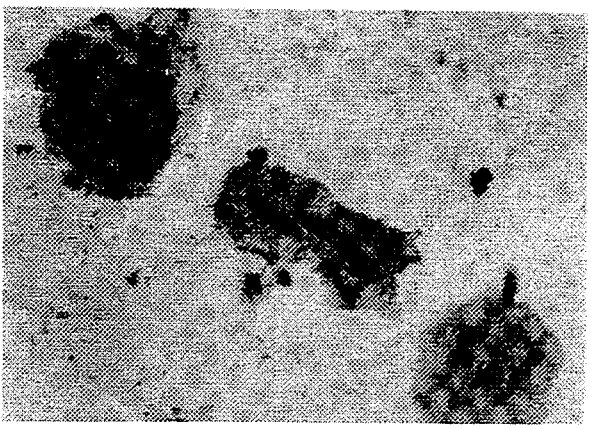
Figure 2C:
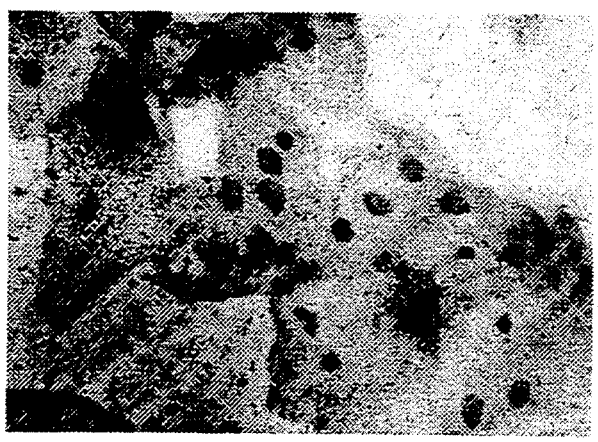

7) Drain the former solution, transfer to the plastic humidified chambers (hybridization boxes) described in FIG. 2, and apply individually prehybridization solution [2× SSC; Blocking Reagent ™ 2% Blocking Reagent. ™ 2% Blocking Reagent (w/v) contains casein from non-fat dry milk, obtained by acid precipitation (acetic acid, pH 4.6) and subsequent solubilization (NaOH, 0.1M) of milk proteins, as referred to by Hölke et al., *Nucleic Acids Res.* 18(9):5843–5851 (1990); 20% formamide (v/v); N-laurylsarcosine, sodium salt, 0.1%(w/v); SDS, 0.02% (w/v)](100 ul per slide). Incubate for 1 hour at 37° C. The solution must be spread to completely cover the cells.

Figure 4:
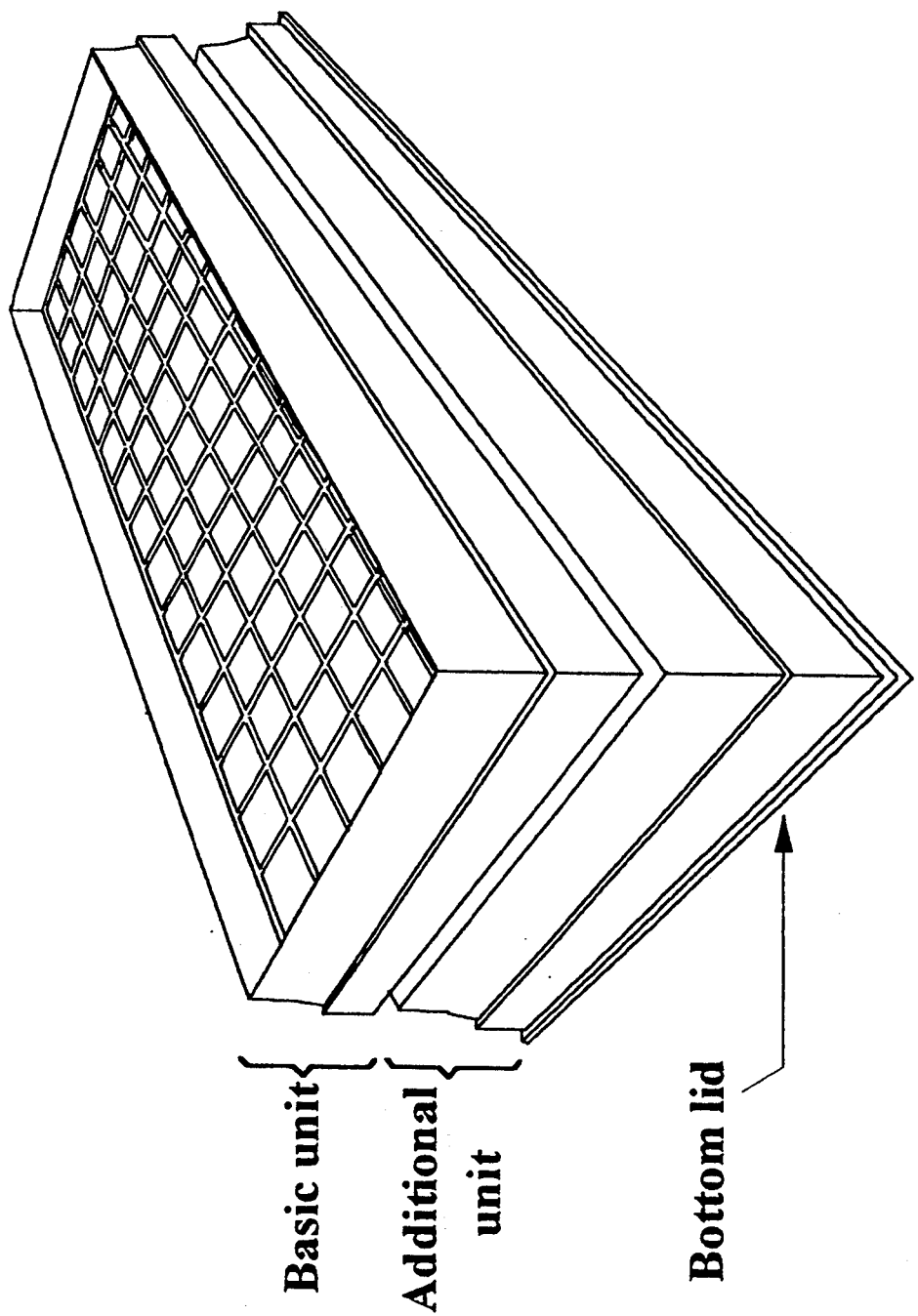
FIG. 4 is a schematic depiction of a hybridization box useful in the invention. The box provides a means for containing the glass slides and solutions during the heating necessary for hybridization.

8) Replace the solution and add the hybridization solution containing the appropriate probe at a concentration of 40 ng/ml. Add 30 ul of the above solution to each slide, still in the hybridization box (FIG. 4), and cover the sample with a coverslip. Finally, seal the edges with rubber cement or nail enamel.

9) Distribute the samples in the hybridization box and incubate at 92° C., i.e., over a boiling water bath, for 10 minutes, remove and then incubate for 1 hour at 37° C.

10) Immerse the slides in a 6× SSC solution at room temperature and detach the coverslip and remove with the help of forceps.

11) Wash once, in a staining jar, with 6× SSC at room temperature, once with 6× SSC at 48° C. and once with 2× SSC at 48° C. All washes for 15 minutes.

Example 2

Probe detection (according to Boehringer's "GENIUS ®" detection Kit)

1) Wash the slides briefly in Buffer 1 (Tris-HCl, 100 mM; NaCl, 150 mM; pH 7.5).

2) Incubate in Blocking solution (0.5% Blocking Reagent ™ in Buffer 1) for 30 minutes.

3) Repeat step 1.

4) Apply 200 ul of the diluted antidigoxigenin-antibody conjugated to alkaline phosphatase (supplied with the kit) to the samples and incubate for 1 hour.

5) Wash four times with Buffer 1 for 15 minutes at room temperature with gentle agitation.

6) Wash once with Buffer 3 (Tris-HCl, 100 mM; NaCl, 100 mM; MgCl₂, 50 mM; pH 9.5) for two minutes at room temperature and drain the excess liquid.

7) Incubate with color-developing solution (45 ul NBT-solution and 35 ul X-phosphate-solution (both solutions supplied with the kit) added to 10 ml of Buffer 3) (500 ul) at room temperature. Keep the slides out of the light in a humidified chamber. Allow to develop for at least 6 hours or overnight.

8) Stop the reaction with Buffer 4 (Tris-HCl, 10 mM; EDTA, 1 mM; pH 8). Dehydrate the samples with graded ethanols (from 70% to 99%). Counterstain with eosin, mount and observe at 40 X magnification in a light microscope. The positive signal will be a dark blue or purplish aggregation in the cell nuclei and propor- 7. The temperature-cycling profile is described below in Table II.

TABLE I

| Forward primers: Target | Primer | Target site |
|---|---|---|
| HPV6 and HPV11 | 5' AGCCCTGTATTGGTT 3' (SEQ ID NO. 3) | |
| HPV16 and HPV18 | 5' ATGGTACAATGGGC 3' (SEQ ID NO. 4) | 1941 |

TABLE II

| Reverse Primers: Target | Primer | Target Site | PCR fragment size |
|---|---|---|---|
| HPV6 | 3' TGCTCGTGCATTAGAATC 5' (SEQ ID NO. 5) | 2007 | 222bp |
| HPV11 | 3' GTTACCTACACTGTCAAC 5' (SEQ ID NO. 6) | 2148 | 363bp |
| HPV16 | 3' GTCATCTATGTAGTTCCAACAG 5' (SEQ ID NO. 7) | 2465 | 524bp |
| HPV18 | 3' TGCATCTTCCTTCTTCCTCGTGC 5' (SEQ ID NO. 8) | 2821 | 809bp | tional to the number of target genomes present.

Figure 3A:
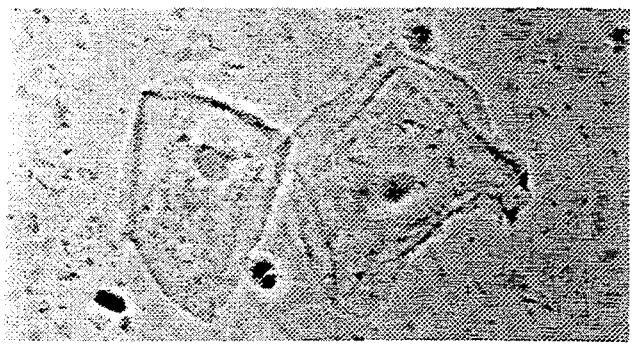
FIG. 3 is a photocopy of a photomicrograph demonstrating the result of an in situ hybridization, performed as in FIG. 2, but complete HPV vital genomes were used as probes. Note the loss of contrast between the positive and negative controls of FIG. 3 in relation to the clear contrast between the same controls in FIG. 2.
Figure 3B:

FIG. 2 shows the results of two positive and one negative case. To compare, FIG. 3 shows the result of the same procedure shown above but using whole viral genomes as probes. Although there is some background staining in the negative case, the positives show very high contrast between the color developed in the nucleus and that in the cytosol. It is the heightened contrast that is indicative of HPV incorporation into the nucleus.

Example 3

PCR Assay

The PCR assay was performed as follows:

1. Cervical or penile epithelial cells were collected by means of a sterile swab and embedded in 0.5 ml of PBS. The samples were kept at 4° C. for no more than 24 hours. Sodium azide (0.1%) was added if samples were stored longer;

2. After brief agitation to transfer the cells from the swab, the latter was discarded and the cells centrifuged for 1-2 minutes in a microcentrifuge;

3. The pelleted cells are washed once with PBS and centrifuged again;

4. The pellet was resuspended in 100 ul of Lysis Solution (50 ug/ml of Proteinase K, 1% Nonidet P40, in water);

5. The sample was incubated for 30 minutes at 65° C. and then at 95° C. for 30 minutes more;

6. 5 ul of the lysed-cell solution is added to a PCR reaction buffer (50 mM KCl; 0.01% gelatin, 1.5% MgCl$_2$, 0.05% Triton-X 100, 200 nM each dNTP, 1 uM each primer, and 2.5 units of *Taq* DNA polymerase) in a final volume of 100 ul. An overlay of mineral oil was used in each reaction to avoid water loss during the cycling;

The temperature-cycling profile used was automatically executed in an Ericomp Single-Block TM System and was cycled as follows:

| Cycle 1: | 10 min. at 95°. (once) |
|---|---|
| Cycle 2: | 30 sec. at 54° C., |
| | 90 sec. at 72° C., 60 sec. at 95° C. (35 times). |
| Cycle 3: | 5 min. at 72° C. (Once). |

The sources of DNA were 2 ng of recombinant plasmids with cloned HPV genomes (positive controls), 100 ng of noninfected human DNA (negative control), 100 ng of DNA purified from patient biopsies, direct lysis of cells obtained from cervical swabs (approximately 150 ng of DNA), and 1 mm$^3$ of tissue from biopsy (200 ng of DNA). The reaction was performed in reaction buffer [50 mM KCl, 0.01% gelatin, 1.5% MgCl$_2$, 0.05% Triton-X 100, 200 nM each dNTP, 1 uM each primer and 2.5 units of Taq DNA polymerase] in a final volume of 100 ul. An overlay of mineral oil was used in each reaction to avoid water loss during the cycling.

Figure 5:
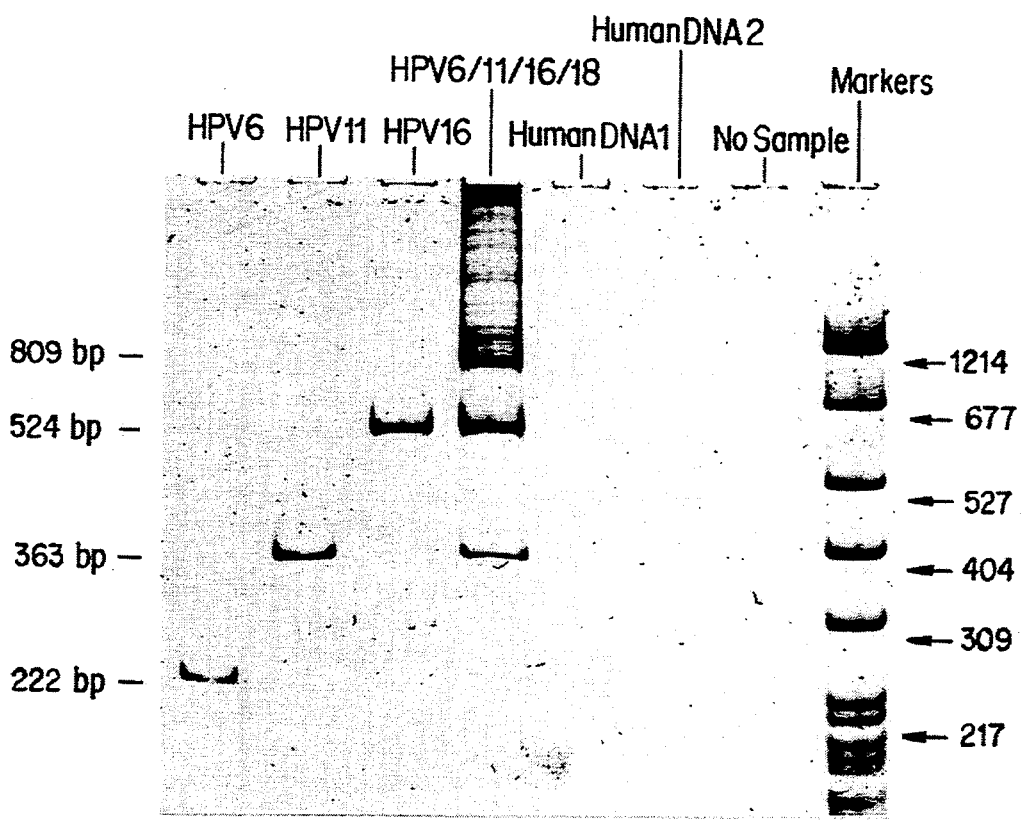
FIG. 5 shows a typical polyacrylamide electrophoretic 6-band pattern of the results of a PCR assay after staining with ethidium bromide. The base-pair sizes of each type-specific reverse primer are indicated in the left column. According to the presence or absence of a PCR amplification product, a determination is made if a patient is infected with HPV, and with which type(s). Additionally, the Figure reveals that the primers are completely compatible and may be used in the same reaction.

It is simple to distinguish the infecting viral types by the sizes of the amplified fragments in an agarose or acrylamide gel electrophoretogram (see FIG. 5). FIG. 5 shows a typical polyacrylamide electrophoretic 6-band pattern of the results of a PCR assay after staining with ethidium bromide. The base-pair sizes of each type-specific reverse primer are indicated in the left column. According to the presence or absence of a PCR amplification product, a determination is made if a patient is infected with HPV, and with which type(s). Additionally, the Figure reveals that the primers are completely compatible and may be used in the same reaction.

Viral type infections may be distinguished by comparing the amplified fragment sizes from the positive cases with the positive control, containing all four HPV types, in the same electrophoretogram.

---

What is claimed is:

1. A polynucleotide molecule comprising the sequence:

5' GAACTTATTACCAGTGTTATACAGG 3' (SEQ ID NO 1), or stably hybridizable fragments thereof, wherein said polynucleotide molecule can simultaneously stably hybridize to human papillomavirus 11 DNA and human Papillomavirus 6 DNA, but cannot stably hybridize to either human papillomavirus 16 DNA or human papillomavirus 18 DNA, and
provided that said polynucleotide molecule is not the entire human papillomavirus 6 genome, or human papillomavirus 11 genome.

2. A polynucleotide molecule consisting essentially of the sequence:

5' ATATCAGATGACGAGRACGAAAATG 3'
(SEQ ID NO. 2), wherein R is A or G, or stably hybridizable fragments thereof, wherein said polynucleotide molecule can simultaneously stably hybridize to human papillomavirus 16 DNA and human papillomavirus 18 DNA, but cannot stably hybridize to either human papillomavirus 6 DNA or human papillomavirus 11 DNA, and
provided that said polynucleotide molecule is not the entire human papillomavirus 16 genome, or human papillomavirus 18 genome.

3. The polynucleotide of any of claims 1 or 2 which is a polydeoxynucleotide.

4. The polynucleotide of any of claims 1 or 2 in detectably labeled form.

5. The polynucleotide of claim 4 wherein said detectably labeled form comprises a label, said label selected from the group consisting of radioactive labels, enzymes, fluorochromes, chemiluminescent agents, antibodies, and biotin.

6. The polynucleotide of claim 4 wherein said detectably labeled form comprises an antigen, said antigen binding specifically to a labeled antibody.

7. The polynucleotide of claim 6 wherein said antigen comprises a deoxynucleotide triphosphate tail attached to said polynucleotide, said dNTP tail having an antigenic moiety attached thereto.

8. The polynucleotide of claim 7 wherein said antigenic moiety comprises digoxigenin.

9. The polynucleotide of claim 6, wherein said labeled antibody comprises an alkaline phosphatase-conjugated anti-digoxigenin antibody.

10. The polynucleotide molecule of claim 4 wherein said detectably labeled form comprises a digoxigenin-deoxyuridine triphosphate tail attached to the 3' terminus of said polynucleotide molecule.

11. The polynucleotide molecule of claim 4 wherein said detectably labeled form comprises a digoxigenin-deoxyuridine triphosphate tail attached to said polynucleotide molecule, in combination with an alkaline phosphatase-conjugated anti-digoxigenin polyclonal antibody.

12. A composition comprising a mixture of the polynucleotide of claim 1 with that of claim 2.

13. The hybridization mixture comprising:

(a) a sample containing human papillomavirus genetic sequences,
(b) a hybridization buffer, and
(c) a detectably labeled probe having the sequence of any one of the polynucleotides of claims 1 or 2, or a mixture of both.

14. The hybridization mixture of claim 13 wherein said detectably labeled probe comprises a label, said label selected from the group consisting of radioactive labels, enzymes, fluorochromes, chemiluminescent agents, antibodies, and biotin.

15. The hybridization mixture of claim 13 wherein said detectably labeled probe comprises an antigen, said antigen binding specifically to a labeled antibody.

16. The hybridization mixture of claim 15 wherein said antigen comprises a deoxynucleotide triphosphate tail attached to said probe, said dNTP tail having an antigenic moiety attached thereto.

17. The hybridization mixture of claim 16 wherein said antigenic moiety comprises digoxigenin.

18. The hybridization mixture of claim 15 wherein said labeled antibody comprises an alkaline phosphatase-conjugated anti-digoxigenin antibody.

19. A method of detecting human papillomavirus in a sample containing or suspected of containing genetic sequences of human papillomavirus, which comprises:
contacting said sample with a detectably labeled probe having the sequences of claim 1 or claim 2, or with a mixture of both, under appropriate hybridization conditions to stably hybridize said probe or probes to said sample, and
detecting said label.

20. The method of claim 19 which is in situ cytohybridization.

21. The method of claim 19 wherein said sample comprises cells of vulval, cervical, or penile origin.

22. A kit compartmentalized to receive in close confinement one or more containers which comprises in combination,
(a) a first container comprising the polynucleotide molecule of claims 1 or 2 or a mixture thereof; and
(b) a second container comprising one or more reagents capable of indicating the presence of said polynucleotide.

23. The kit of claim 22 wherein said reagents capable of indicating the presence of said polynucleotide comprise a detectable label.

24. The kit of claim 23 wherein said detectable label is selected from the group consisting of radioactive labels, enzymes, fluorochromes, chemiluminescent agents, antigens, antibodies, and biotin.

25. The kit of claim 24 wherein said antigen comprises a deoxynucleotide triphosphate tail attached to said polynucleotide, said dNTP tail having an antigenic moiety attached thereto.

26. The kit of claim 25 wherein said antigenic moiety comprises digoxigenin.

27. The kit of claim 24 wherein said antibody is conjugated to a detectable label and binds specifically to an antigenic moiety of claim 28.

28. The kit of claim 27 wherein said labeled antibody comprises an alkaline phosphatase-conjugated anti-digoxigenin antibody.

* * * * *